United States Patent
Parr et al.

(10) Patent No.: US 6,322,778 B1
(45) Date of Patent: Nov. 27, 2001

(54) HAIR CONDITIONING COMPOSITIONS COMPRISING A QUATERNARY AMMONIUM COMPOUND

(75) Inventors: Deborah J. Parr, Pine Brook, NJ (US); Jun Li, Shanghai (CN)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 09/245,138

(22) Filed: Feb. 4, 1999

Related U.S. Application Data

(60) Provisional application No. 60/074,249, filed on Feb. 10, 1998.

(51) Int. Cl.[7] .............................. A61K 7/06; A61K 7/00; A61K 7/08
(52) U.S. Cl. .................. 424/70.28; 424/47; 424/70.1; 424/70.11; 424/70.12; 424/70.31; 510/119; 510/122
(58) Field of Search .................. 424/70.28, 47, 424/70.1, 70.11, 70.31, 70.12; 510/122, 119

(56) References Cited

U.S. PATENT DOCUMENTS

| | | |
|---|---|---|
| 3,990,991 | 11/1976 | Gerstein . |
| 4,337,166 | 6/1982 | Hill et al. . |
| 4,374,825 | 2/1983 | Bolich, Jr. et al. . |

(List continued on next page.)

FOREIGN PATENT DOCUMENTS

| | | |
|---|---|---|
| 1153312 | 9/1983 | (CA) . |
| 1155396 | 10/1983 | (CA) . |
| 1155397 | 10/1983 | (CA) . |

(List continued on next page.)

OTHER PUBLICATIONS

K. Gallagher, Cosmetics and Toiletries, 109(12) pp 67–70, Dec. 1994.*
RD 396001A (1997–Abstract).
JP 1006207A (1989–Abstract).
JP 52072834A (1981–Abstract).
JP 63264515A (1988–Abstract).
JP 63222110A (1988–Abstract).
JP 1258615A (1988–Abstract).
JP 52151737A (1977–Abstract).
JP 63130515A (1988–Abstract).
EP 80977A (1983–Abstract).
AU–A–77246/91 (1991–Abstract).
AU–B–17501/88 (1988–Abstract).

(List continued on next page.)

*Primary Examiner*—Thurman K. Page
*Assistant Examiner*—Brian K. Seidlech

(57) ABSTRACT

The present invention relates to hair conditioning or detailing compositions comprising from about 0.01 percent to about 2.0 percent by weight of a quaternary ammonium compound of the formula:

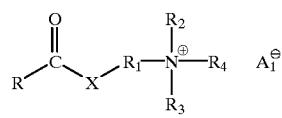

and from about 0.01 percent to about 2.0 percent by weight of a silicone compound, wherein R is a substituted or unsubstituted alkyl or alkenyl group having from about 11 to about 35 carbon atoms, X is —O—or N—$R_5$, $R_1$ is a substituted or unsubstituted alkylene group having from about 2 to about 6 carbon atoms, $R_2$, $R_3$ and $R_4$ are each independently an alkyl or hydroxyalkyl group having from about 1 to about 4 carbon atoms, $R_5$ is H or $CH_3$, and $A_1$ is chloride; bromide; alkylsulfate containing from about one to about two carbon atoms; or mixtures thereof.

24 Claims, 1 Drawing Sheet

U.S. PATENT DOCUMENTS

| | | |
|---|---|---|
| 4,387,090 | 6/1983 | Bolich, Jr. . |
| 4,472,375 | 9/1984 | Bolich, Jr. et al. . |
| 4,591,610 | 5/1986 | Grollier . |
| 4,711,776 | 12/1987 | Suzuki et al. . |
| 4,777,037 | 10/1988 | Wagman et al. . |
| 4,784,844 | 11/1988 | Thimineur et al. . |
| 4,818,523 | 4/1989 | Clarke et al. . |
| 4,822,511 | 4/1989 | Law . |
| 4,859,457 | 8/1989 | Suzuki et al. . |
| 4,892,728 | 1/1990 | Kawa et al. . |
| 4,902,499 | 2/1990 | Bolish, Jr. et al. . |
| 4,910,013 | 3/1990 | Kanamaru et al. . |
| 4,950,468 | 8/1990 | Nakamura et al. . |
| 4,954,335 | 9/1990 | Janchipraponvej . |
| 4,973,476 | 11/1990 | Krzysik . |
| 4,976,956 | 12/1990 | Noe . |
| 5,002,762 | 3/1991 | Bolich, Jr. . |
| 5,248,445 | 9/1993 | Rizvi et al. . |
| 5,277,899 | * 1/1994 | McCall . |
| 5,288,484 | 2/1994 | Tashjian . |
| 5,290,555 | 3/1994 | Guthauser et al. . |
| 5,334,376 | 8/1994 | Robbins et al. . |
| 5,374,421 | 12/1994 | Tashiro et al. . |
| 5,441,667 | 8/1995 | Tonomura et al. . |
| 5,456,863 | 10/1995 | Bergmann . |
| 5,478,553 | 12/1995 | Chandran et al. . |
| 5,632,977 | 5/1997 | Chandran et al. . |
| 5,726,137 | * 3/1998 | Patel et al. . |
| 6,020,303 | * 2/2000 | Cripe et al. . |

FOREIGN PATENT DOCUMENTS

| | | |
|---|---|---|
| 1212332 | 10/1986 | (CA) . |
| 2264660 | 1/1990 | (CA) . |
| 2019816 | 1/1991 | (CA) . |
| 2031020 | 6/1991 | (CA) . |
| 2071637 | 6/1991 | (CA) . |
| 2042980 | 11/1991 | (CA) . |
| 2019809 | 12/1991 | (CA) . |
| 2042693 | 12/1991 | (CA) . |
| 2048775 | 4/1992 | (CA) . |
| 2058361 | 6/1992 | (CA) . |
| 1309353 | 10/1992 | (CA) . |
| 1309354 | 10/1992 | (CA) . |
| 1330689 | 7/1994 | (CA) . |
| 2114605 | 10/1994 | (CA) . |
| 2161762 | 6/1996 | (CA) . |
| 2163854 | 7/1996 | (CA) . |
| 1338798 | 12/1996 | (CA) . |
| 0 166 611 | 1/1986 | (EP) . |
| 0 080 976 | 9/1986 | (EP) . |
| 0 194 146B2 | 9/1986 | (EP) . |
| 0 080 977 | 11/1986 | (EP) . |
| 0 460 683A2 | 12/1991 | (EP) . |
| 0 511 652 B1 | 11/1992 | (EP) . |
| 0 566 049 A1 | 10/1993 | (EP) . |
| 0 654 259 A1 | 5/1995 | (EP) . |
| 2074 184B | 10/1981 | (GB) . |
| 2 102 288B | 2/1983 | (GB) . |
| 2 205 743B | 12/1988 | (GB) . |
| 91/07395 | 5/1991 | (WO) . |
| 93/00892 | 1/1993 | (WO) . |
| 93/02666 | 2/1993 | (WO) . |
| 93/07848 | 4/1993 | (WO) . |
| 93/13750 | 7/1993 | (WO) . |
| 94/14404 | 7/1994 | (WO) . |
| 95/01151 | 1/1995 | (WO) . |
| 95/20939 | 8/1995 | (WO) . |
| 95/27033 | 10/1995 | (WO) . |
| 96/03970 | 2/1996 | (WO) . |
| 96/15217 | 5/1996 | (WO) . |
| 96/25917 | 8/1996 | (WO) . |
| 96/28008 | 9/1996 | (WO) . |
| 96/32089 | 10/1996 | (WO) . |
| 97/03647 | 2/1997 | (WO) . |
| 97/07195 | 2/1997 | (WO) . |
| 97/07774 | 3/1997 | (WO) . |

OTHER PUBLICATIONS

AU–A–57688/90 (1990–Abstract).
AU–B–33945/89 (1989–Abstract).
AU–A–32329/89 (1989–Abstract).
AU–B–31409/89 (1989–Abstract).
AU–B–24058/88 (1988–Absract).
AU–B–83271/87 (1988–Abstract).
AU–B–28865/89 (1989–Abstract).
AU–B–65519/94 (1994).
AU–B–64971/80 (1984 Abstract).
AU–B–57854/90 (1990 Abstract).
AU–B–83162/82 (1986 Abstract).
AU–B–88547/91 (1991 Abstract).
AU–A–19511 (1992 Abstract).
AU–B–65501/94 (1994 Abstract).
Dow Corning Corp., Material Safety Data Sheet (344 Fluid) (12/96).
Material Safety Data Sheet, Incroquat Behenyl He, Croda, Inc. (Sep. 28, 1995).
Material Safety Data Sheet, Incroquat Behenyl TMS, Croda, Inc. (Dec. 15, 1992).
Data (Incroquat Behenyl TMS) (Jun. 1, 1994).
Data Incroquat Behenyl He (May 8, 1996).

* cited by examiner

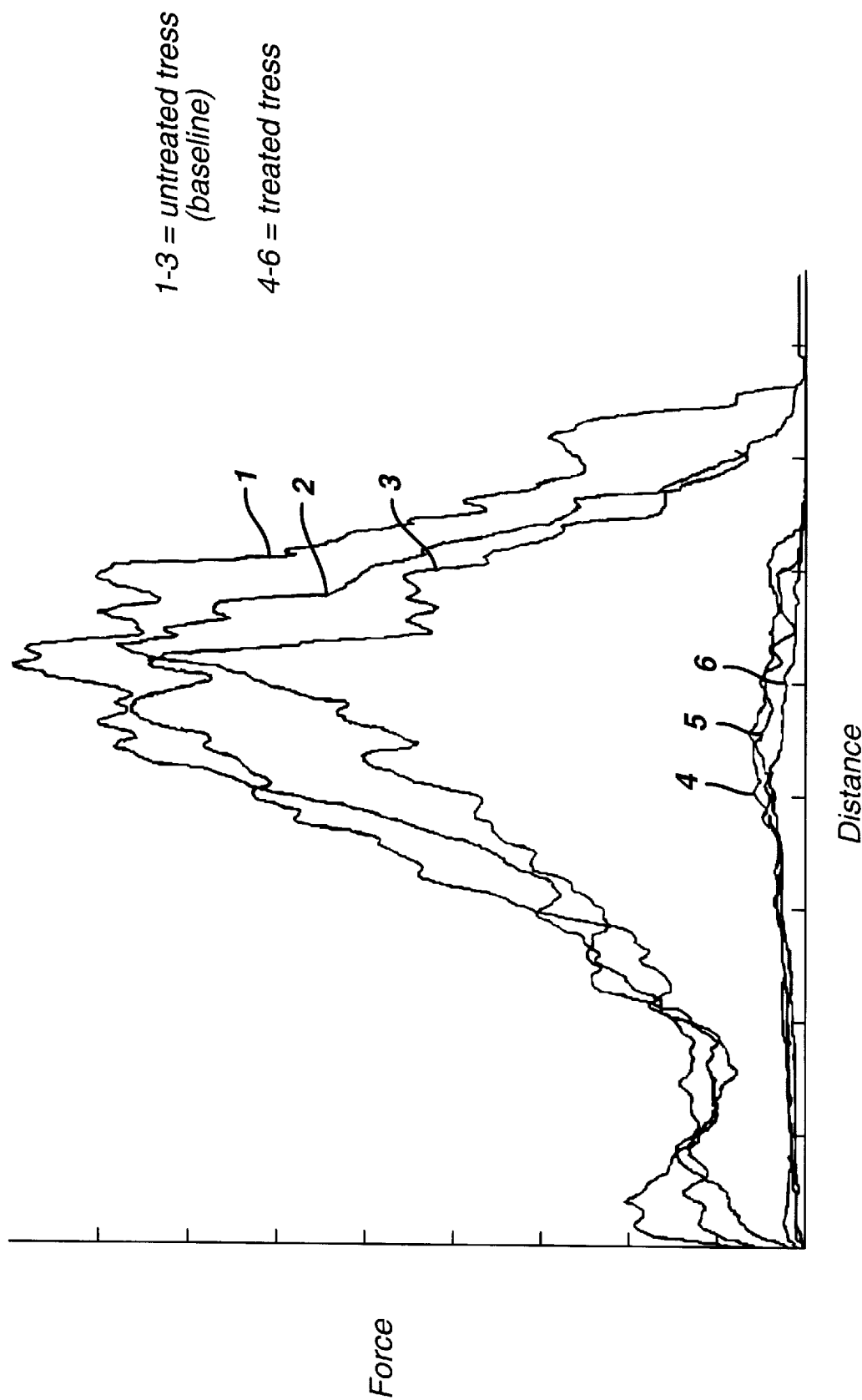

HAIR CONDITIONING COMPOSITIONS COMPRISING A QUATERNARY AMMONIUM COMPOUND

CROSS-REFERENCE TO RELATED APPLICATION

This Application claims the benefit of U.S. Provisional Application No. 60/074249 filed on Feb. 10, 1998 now abandoned, which is incorporated herein by reference in its entirety.

FIELD OF THE INVENTION

The present invention relates to compositions that are useful in conditioning hair, especially in the form of a leave-on hair conditioner or hair derange.

BACKGROUND

Compositions that can be used to condition hair are well known. Hair conditioning compositions are intended to leave the hair manageable, soft, and shiny. Manageability is manifested as ease of combing in the wet and dry states, as well as preventing hair "fly-away" in the dry state. Most hair conditioning compositions are applied to the hair when wet, usually as an after-treatment following shampooing. More recently, two-in-one conditioning shampoos have been developed which provide cleansing and conditioning of the hair with a single composition. Both the after-treatment conditioners and the two-in-one shampoos are usually rinsed off after being allowed to remain in contact with the hair for a brief period of time, and hence, are referred to in the art as "rinse off" type compositions. While the hair conditioning compositions of the present invention may be used in rinse-off products, they are particularly directed to a "leave-on" product, i.e., one which is applied to the hair in either a wet or dry state, and is not subsequently rinsed off. Such leave-on products are typically applied to the hair from a pump-type spray dispenser in a form ranging from a mist to a liquid stream.

U.S. Pat. No. 4,374,825 discloses hair conditioning compositions comprising from about 1 to about 13% of a volatile liquid hair conditioning agent selected from hydrocarbons and silicones, from 0.1 to about 8% of a water soluble nonionic polymer thickening agent and from about 0.05 to about 4% of a cationic agent selected from quaternary ammonium salts or salts of fatty amines. The compositions of the '825 patent are in the form of emulsions.

U.S. Pat. No. 4,387,090 discloses hair conditioning compositions comprising from 1 to 99% volatile hydrocarbon or silicone and up to about 1% of a hydrophobic polymeric thickening agent. The composition optionally comprises up to about 4% of a cationic conditioning agent selected from quaternary ammonium salts and salts of fatty amines.

U.S. Pat. No. 4,711,776 disposes hair cosmetic compositions comprising 0.01 to about 20% branched quaternary ammonium salts and 0.1 to 30% oils and fats selected from higher alcohols and fatty acid monoglycerides.

U.S. Pat. No. 4,777,037 discloses hair conditioning compositions comprising 1 to 4% polydimethyl cyclosiloxane and 0.5 to 5% of a quaternary nitrogen-containing conditioning agent having two long chain alkyl groups, each of said alkyl groups having from 12 to 18 carbon atoms. Preferred compositions are said to further comprise 0.5 to 10% fatty alcohol and 0.1 to 2% of a tertiary amidoamine. The compositions of this patent are in the form of emulsions.

U.S. Pat. No. 4,784,844 discloses silicone emulsions comprising 100 parts by weight cyclic siloxane; from 0.7 to 666 parts emulsifier selected from ethoxylated fatty acids, ethoxylated and non-ethoxylated sorbitan esters, ethoxylated alkyl phenols and ethoxlated ethers; and from 5 to 960 parts water, all parts being in parts by weight. The emulsions are said to be useful for cosmetic and medicinal purposes.

U.S. Pat. No. 4,859,457 discloses hair rinse compositions comprising 0.05 to 0.5% of a cationic surface active agent and a second component selected from higher alcohols and monoglycerides, said second component being present in the composition at 3 to 15 times the weight of the cationic surface active agent.

U.S. Pat. No. 4,982,728 is directed to pumpable cationic fatty alcohol dispersions said to have application in cosmetic hair care and skin care preparations. The dispersions comprise from 10 to 25% by weight of a fatty alcohol and from 0.01 to 1% by weight of a cationic surface active compound.

U.S. Pat. No. 4,902,499 discloses hair conditioner compositions comprising from 0.01 to 10% of a rigid silicone polymer and a volatile carrier. In some embodiments, the compositions additionally comprise from 0.1 to 10% of a lipid vehicle material (preferably selected from fatty alcohols, fatty esters and monoglycerides) and from 0.05 to 5% of a cationic surfactant (preferably a di-fatty alkyl quaternary ammonium compound).

U.S. Pat. No. 4,910,013 discloses hairdressing compositions comprising branched alkyl quaternary ammonium compounds and silicone compounds.

U.S. Pat. No. 4,950,468 discloses a hair treating composition comprising from 0.05 to 2.5% of a dimethyl silicone rubber and from 0.1 to 5.0% of a mixture of stearyl trimonium chloride and behenyl trimonium chloride. The components of the composition are said to adsorb strongly to hair and they are not readily desorbed, even by washing.

U.S. Pat. No. 4,954,335 discloses a hair conditioning composition comprising from 0.1 to 5% of a quaternary ammonium compound (preferably containing two fatty alkyl groups), from 0.1 to 5% of an amidoamine, from 0.5 to 5% of a volatile conditioning compound selected from silicone and aliphatic hydrocarbon, from 1 to 10% of a non-ionic surfactant, preferably, a fatty alkyl pyrolidone, and from 10 to 30% of a polyhydric alcohol, all in a suitable liquid vehicle.

U.S. Pat. No. 4,973,476 discloses leave-on hair conditioning compositions comprising 75 to 99.9% volatile silicone and from 0.1 to 10% of at least one functional silicone. The compositions may further comprise optional ingredients such as anti-static agents, organic esters and surfactants, among others.

U.S. Pat. No. 4,976,956 discloses hair-treating compositions comprising at least 0.35% of a water-soluble quaternary ammonium compound, from 0.4 to 15% of an oil soluble, water-dispersible quaternary ammonium compound, from 0.1 to 5% of an acid-neutralized amidoamine, from 0.1 to 2% of a polydimethylsiloxane and a suitable liquid vehicle. The compositions may further contain optional ingredients such as organic cosolvents, illustrative members including lower alcohols, glycols and polyols. Other optional ingredients include long chain fatty alcohols. The compositions are said to be useful either in leave-on or in rinse off products.

U.S. Pat. No. 5,002,762 discloses hair conditioning compositions comprising 0.5 to 12% of particular volatile silicone compounds, 0.5 to 3% of a lipid vehicle material such as fatty alcohols or fatty esters, and 0.2 to 4% of a cationic surfactant.

U.S. Pat. No. 5,288,484 discloses a pre-shampoo conditioning composition comprising from 0.1 to 20% of a particular cationic cellulose, from 0.05 to 20% of a poly (allyidimethylammonium) polymer and from 0.2 to 10% of behenamidopropyl dihydroxypropyl dimonium chloride.

U.S. Pat. No. 5,290,555 discloses a hair conditioner comprising an oil phase and an aqueous phase. The oil phase comprises a variety of volatile and non-volatile silicone components. The aqueous phase comprises olealkonium chloride and PEG-8.

U.S. Pat. No. 5,374,421 discloses hair treatment compositions comprising 0.1 to 10% of a silicone polymer having at least one alkoxy group containing 12 to 22 carbon atoms, said polymer having a melting point of not less than 30° C.; 0.1 to 20% of a cationic surface active agent; 0.1 to 30% of an alcohol having from 12 to 26 carbon atoms; 0.1 to 90% of a water-compatible organic alcohol; and water.

WO 97/07774 discloses a hair treatment composition particularly useful as a rinse-off product that comprises 0.6 to about 10% of a fatty alcohol, 0.01 to 15% of a silicone conditioning agent and from 0.1 to 5% of a monoalkyl trimethylammonium salt. The silicone conditioning agent is preferably non-volatile, and the ammonium salt is preferably behenyl trimethylammonium chloride.

While a number of the above references disclose the combination of silicones and quaternary ammonium salts, we are unaware of any references that disclose hair care compositions that incorporate a silicone compound in conjunction with a fatty quaternary ammonium compound wherein the fatty group is an acyl group, derived, for example, from an amide or ester.

There are a number of important requirements for a leave-on conditioner composition. First, the composition must impart the desired conditioning benefits of manageability, softness and shine. Second, the product should be physically and chemically stable. Third, the composition should be mild and non-irritating to the skin and eyes. This property is especially important when the composition is used on children. Fourth, the product should leave minimal residue on the hair. Finally, the composition should have physical properties such as viscosity that permit its application from a spray dispenser.

Accordingly, one object of the present invention is a conditioning composition that delivers the requisite benefits of hair manageability, softness and shine.

Another object of the invention is to provide a composition that delivers the requisite conditioning benefits and is both physically and chemically stable.

Another object of the invention is to provide a composition that delivers the requisite conditioning benefits and is mild and non-irritating to the skin and eyes.

Another object of the invention is to provide a composition that delivers the requisite conditioning benefits and can be applied to and left on the hair without leaving appreciable residue on the hair.

Another object of the invention is to provide a composition that delivers the requisite conditioning benefits and can be applied to the hair in a variety of physical forms, including a spray.

SUMMARY OF THE INVENTION

The present invention relates to a hair conditioning composition which comprises, based upon the total weight of the composition:

A. about 0.01 percent to about 2.0 percent of a quaternary ammonium compound of the formula

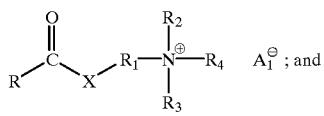

B. about 0.01 percent to about 2.0 percent of a silicone compound wherein
R is a substituted or unsubstituted alkyl or alkenyl group having from about 11 to about 35 carbon atoms,
X is —O— or N—$R_5$,
$R_1$, is a substituted or unsubstituted alkylene group having from about 2 to about 6 carbon atoms,
$R_2$, $R_3$ and $R_4$ are each independently an alkyl or hydroxyalkyl group having from about 1 to about 4 carbon atoms,
$R_5$ is H or $CH_3$, and
$A_1$ is chloride; bromide; alkylsulfate containing from about one to about two carbon atoms; or mixtures thereof.

In a preferred embodiment, the invention relates to a conditioning composition comprising:

A. a first quaternary ammonium compound of the formula

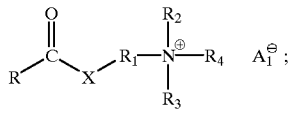

B. a second quaternary ammomni compound of the formula

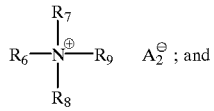

C. based upon the total weight of the composition, from about 0.01 percent to about 2.0 percent of a silicone compound wherein
R is a substituted or unsubstituted alkyl or alkenyl group having from about 11 to about 35 carbon atoms,
X is —O— or N—$R_5$,
$R_1$ is a substituted or unsubstituted alkylene group having from about 2 to about 6 carbon atoms,
$R_2$, $R_3$ and $R_4$ are each independently an alkyl or hydroxyalkyl group having from about 1 to about 4 carbon atoms,
$R_5$ is H or $CH_3$,
$R_6$ is an alkyl or alkenyl group having from about 12 to about 36 carbon atoms,
$R_7$ is an alkyl or alkenyl group having from about one to about 36 carbon atoms or a benzyl group,
$R_8$ and $R_9$ are each independently an alkyl group having from about 1 to about 4 carbon atoms or a benzyl group,
$A_1$ and $A_2$ are each independently chloride; bromide; alkylsulfate containing from about one to about two carbon atoms; or mixtures thereof, and wherein said first and said second quaternary ammonium compounds together comprise between about 0.01 percent to about 2.0 percent by weight of said composition.

Another preferred embodiment of the invention relates to a hair conditioning composition comprising:

A. a first quaternary ammonium compound of the formula

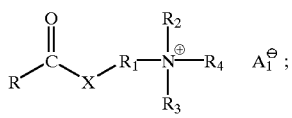

B. a second quaternary ammonium compound of the formula

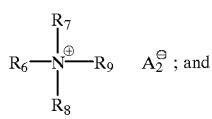

C. based upon the total weight of the composition, from about 0.01 to about 2.0 percent by weight of a volatile silicone compound wherein R is an alkyl or alkenyl group having from about 17 to about 21 carbon atoms, X is —O— or N—H, $R_1$ is a substituted or unsubstituted alkylene group having from about 2 to about 6 carbon atoms, $R_2$, $R_3$ and $R_4$ are each independently an alkyl or hydroxyalkyl group having from about 1 to about 4 carbon atoms, $R_6$ is an alkyl or alkenyl group having from about 18 to about 22 carbon atoms, $R_7$, $R_8$ and $R_9$ are each independently an alkyl group having from about 1 to about 4 carbon atoms or a benzyl group, $A_1$ and $A_2$ are each independently chloride; bromide; alkylsulfate containing from about one to about two carbon atoms; or mixtures thereof, and wherein said first and said second quaternary ammonium compounds together comprise between about 0.01 to about 2.0 percent by weight of said composition.

Another embodiment of the invention relates to a conditioning composition comprising, based upon the total weight of the composition:

A. from about 0.05 percent to about 1.0 percent of a first quaternary ammonium compound of the formula

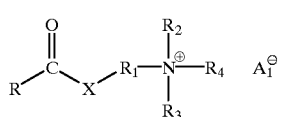

B. from about 0.05 percent to about 1.0 percent of a second quaternary ammonium compound of the formula

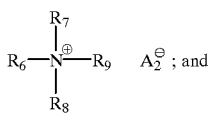

C. from about 0.05 to about 1.0 percent of a volatile silicone compound having from about 4 to about 6 silicon atoms, wherein R is an alkyl group having about 21 carbon atoms, X is N—H, $R_1$ is a substituted or unsubstituted alkylene group having from about 2 to about 6 carbon atoms, $R_2$, $R_3$ and $R_4$ are each independently an alkyl or hydroxyalkyl group having from about 1 to about 4 carbon atoms, $R_6$ is an alkyl group having about 22 carbon atoms, $R_7$, $R_8$ and $R_9$ are each independently $CH_3$, $A_1$ and $A_2$ are each independently chloride; bromide; alkylsulfate containing from about one to about two carbon atoms; or mixtures thereof.

BRIEF DESCRIPTION OF THE DRAWINGS

FIG. 1 is a graph showing the comb force for a tress treated with the composition according to Example 2.

DETAILED DESCRIPTION OF THE INVENTION

In a first embodiment, the invention relates to hair conditioning compositions comprising a quaternary ammonium compound of the formula

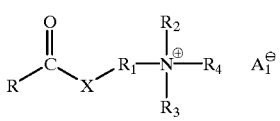

wherein

R is a substituted or unsubstituted alkyl or alkenyl group having from about 11 to about 35 carbon atoms;

X is —O— or N—$R_5$;

$R_1$ is an alkylene group having from about 2 to about 6 carbon atoms, said alkylene group being unsubstituted or substituted, e.g., with a functional group such as a hydroxyl group;

$R_2$, $R_3$ and $R_4$ are each independently an alkyl or hydroxyalkyl group having from about 1 to abut 4 carbon atoms. Illustrative hydroxyalkyl groups being hydroxyethyl, hydroxypropyl or dihydroxypropyl;

$R_5$ is H or $CH_3$; and $A_1$ is chloride; bromide; alkylsulfate containing from about one to about two carbon atoms; or mixtures thereof.

It is well known in the art that long chain functional hydrocarbons are materials that occur in nature as mixtures of varying chain length. Accordingly, in the case of refined materials, R may represent a group having a single chain length. Alternatively, in the case of less refined materials, R may represent a material having a mixture of different chain lengths within the broadest prescribed range.

In a preferred embodiment, the quaternary ammonium compound I has the structure shown hereinabove wherein R is an alkyl group having from about 17 to about 21 carbon atoms, preferably from about 19 carbon atoms to about 21 carbon atoms, and more preferably about 21 carbon atoms, or mixtures thereof; X is an N—$R_5$ group; $R_5$ is H and the other structural elements are as hereinabove defined. The composition of the invention comprises, based upon the total weight of the composition, from about 0.01 percent to about 2.0 percent, preferably from about 0.05 percent to about 1.0 percent, and more preferably from about 0.1 to about 0.5 percent by weight of the quaternary ammonium compound. Exemplary materials useful as the quaternary ammonium compound in the compositions of the invention include compounds having the formula II through V below.

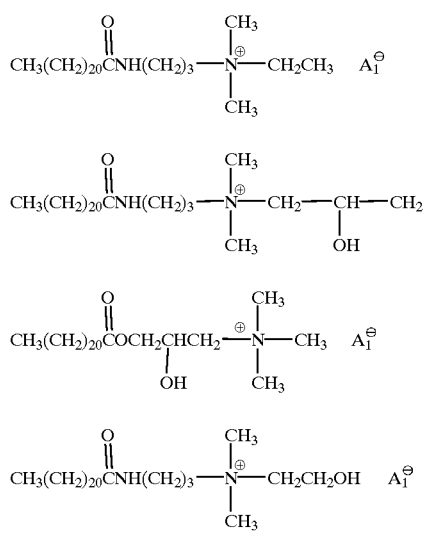

The compound of formula II wherein $A_1$ is ethosulfate is available as "Schercoquat BAS" from Scher Chemicals, Inc. of Clifton, N.J. The compound of formula III wherein $A_1$ is chloride is available as "Lexquat AMG-BEO" from Inolex Chemical Co. of Philadelphia, Pa. The compound of formula IV wherein $A_1$ is chloride is available as "Akypoquat 131" from Chemische Fabrik Chem-Y of Emmerich, Germany. The compound of formula V wherein $A_1$ is chloride is available as "Incroquat Behenyl HE" from Croda, Inc. of Parsippany, N.J. The latter material, which is a 50% mixture of the compound of formula V in hexylene glycol, is a preferred source of the quaternary ammonium compound useful in the compositions of the invention.

The compositions of the invention further comprise, based upon the total weight of the composition, from about 0.01 percent to about 2.0 percent, and preferably from about 0.05 percent to about 1.0 percent of an organic silicone compound. Preferably, suitable silicone compounds are in the form of a fluid or a gum. Silicone compounds useful in the compositions of the invention include, but are not limited to dimethicones, which are a mixture of fully methylated linear siloxane polymers end blocked with trimethylsiloxy units; cydomethicones, which are cydic dimethyl polysiloxane compounds having from about 3 to about 6 silicon atoms; and mixtures thereof.

The organic silicone compounds useful in the compositions of the invention are preferably volatile, i.e., they have a boiling point below about 250° C. The cyclomethicones having between about 4 and about 6 silicon atoms are especially useful in this regard. An exemplary material useful in the compositions of the invention is "Dow Coming 344 Fluid," available from Dow Coming of Midland, Mich. This material consists of about 77% by weight octamethyl-cydotetrasiloxane and about 22% by weight decamethylpentasiloxane.

In another embodiment, the invention relates to hair conditioning compositions comprising a mixture of at least two cationically charged quaternary ammonium compounds. The first of these quaternary ammonium compounds is of formula I as described hereinabove. The second quaternary ammonium compound has the structure:

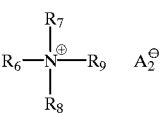

Wherein $R_6$ is an alkyl or alkenyl group having from about 12 to about 36 carbon atoms, $R_7$ is an alkyl or alkenyl group having from about 1 to about 36 carbon atoms or a benzyl group, $R_8$ and $R_9$ are each independently an alkyl group having from about 1 to about 4 carbon atoms or a benzyl group, $A_2$ is chloride; bromide; alkylsulfate containing from about one to about two carbon atoms; or mixtures thereof.

As was the case with the R group in the compound of formula I, $R_6$ and $R_7$ may represent groups with a single chain length or a material containing a mixture of different chain lengths.

The second quaternary ammonium compound may contain one or two fatty chains, but materials containing one fatty alkyl chain are preferred.

In a preferred embodiment, the substituents about the nitrogen atom of the second quaternary ammonium compound are as follows:

$R_6$ is an alkyl or alkenyl group having from about 18 to about 22 carbon atoms, preferably from about 20 to about 22 carbon atoms, and more preferably about 22 carbon atoms, and $R_7$, $R_8$ and $R_9$ are each independently an alkyl group having from about 1 to about 4 carbon atoms or a benzyl group, and more preferably a methyl group.

Exemplary materials useful as the second quaternary ammonium compound in the compositions of the invention include, but are not limited to behenalkonium chloride, available from Hoechst Celanese Company of Charlotte, N.C. under the tradename of "Genamin KDB", dibehenyi-dimonium chloride, available from Witco Corp. of Dublin Ohio as "Kemamine Q-2802C," dibehenyldimonium methosulfate available from Croda, Inc. of Parsippany, N.J. under the tradename "Incroquat DBM-90," dibehenylidiarachidyl dimonium chloride available from Witco as "Kemamine Q-1902C," behentrimonium chloride available from Hoechst Celanese as "Genamin KDM," behentrimonium methosulfate available from Croda, Inc. under the tradename "Incroquat Behenyl TMS," and mixtures thereof. The latter material is a mixture containing 25% behentrimonium methosulfate and 75% cetearyl alcohol, and is an especially preferred raw material for the second quaternary ammonium compound in the compositions of the invention.

When both of the above-described two quaternary ammonium compounds, i.e., the compounds of formula I and formula VI, are present in the compositions of the invention, they together comprise, based upon the total weight of the composition, between about 0.01 percent to about 2.0 percent, preferably between about 0.05 percent to about 1.0 percent, and more preferably between about 0.1 percent to about 0.5 percent of the composition. The weight ratio of the first quaternary ammonium compound to the second quaternary ammonium compound is preferably in the range of about 4:1 to about 1:4, and is most preferably in the range of about 2:1 to about 1:2.

The compositions of the invention may further comprise additional components such as glycols or polyols, surfactants, and fatty alcohols. Exemplary glycols include, but are not limited to propylene glycol, butylene glycol, hexylene glycol, and mixtures thereof. An exemplary polyol useful in the compositions is glycerine.

The compositions of the invention may be in the form of a conditioning shampoo, a rinse-off conditioner, a leave-on conditioner or a hair derange. The compositions are preferably in the form of a leave-on conditioner.

When in the form of a shampoo, the compositions of the invention typically contain surfactants at a concentration required to clean the hair, totaling in the range of about 5 percent to about 20 percent by weight of the composition. The surfactants in shampoo compositions may include anionic, nonionic or amphoteric surfactants, or mixtures of these surfactants. When in the form of a leave-on conditioner, the compositions of the invention preferably comprise a relatively smaller amount of a non-ionic surfactant typically in the range of about 0.01 percent to about 1.0 percent by weight of the composition. Exemplary classes of nonionic surfactants useful in leave-on conditioners comprising the compositions of the invention include, but are not limited to the alkoxylated alcohols and alkoxylated polyol esters. Preferably, the nonionic surfactants are ethoxylated alcohols, ethoxylated polyol esters, or mixtures thereof. Exemplary materials useful in this regard include ethoxylated lanolin and ethoxylated sorbitan esters. An exemplary ethoxylated lanolin useful in the compositions of the invention is PEG60 lanolin, available as "Solan 50" from Croda, Inc. An exemplary ethoxylated sorbitan ester useful in the compositions of the invention is polyoxyethylene (20) sorbitan monolaurate, available as "Tween 20" from ICI Surfactants of Wilmington, Del.

When in the form of a leave-on conditioner, the compositions may also comprise, based upon the total weight of the composition, from about 0.01 percent to about 1.0 percent of a fatty alcohol having from about 12 to about 36 carbon atoms. Exemplary fatty alcohols include, but are not limited to lauryl alcohol, cetyl alcohol, stearyl alcohol, behenyl alcohol, and mixtures thereof.

When in the form of a product other than a shampoo, i.e. a leave-on conditioner or derange, the composition preferably is substantially free of any anionic surfactants. By "substantially free," it is meant that the composition contains no more than 0.5 weight %, and preferably no more than 0.1 weight % of anionic surfactants.

The compositions may further comprise optional functional ingredients such as buffering agents, preservatives and fragrances.

For maximum convenience to the consumer, the package which contains the composition of the invention is preferably a dispensing package such as a spray dispenser or a foam dispenser. When the composition of the invention is in the form of a leave-on conditioner or a hair derange, it is preferably contained in a spray dispenser package. Such packages contain a piston pump by which the composition is dispensed in the form of a mist, droplets or a stream of liquid As such, leave-on conditioners or hair detanglers comprising the compositions of the invention should have relatively low viscosity to permit the compositions to be readily dispensed via such pump dispensers.

The compositions of the invention are especially useful in hair derange products, where they facilitate the detailing of tangled hair by reducing the force required to comb tangled hair as discussed hereinabove. The compositions may be used either when the hair is wet or dry. If the hair is wet, it is preferable that excess water be squeezed from the hair, and that the compositions of the invention be uniformly applied to the hair, as for example, from a spray dispenser. The composition may then be worked into the hair and the hair may then be combed or brushed. Alternatively, for use on dry hair, the compositions should be applied to the hair until the hair becomes damp and then the hair is combed or brushed.

Several examples are set forth below to further illustrate the nature of the invention and the manner of carrying it out. However, the invention should not be considered as being limited to the details thereof.

EXAMPLE 1

A hair derange composition having formula shown in Table I was prepared as follows:

TABLE 1

Formula of Example 1

| Ingredient | Ingredient Amount (%) | Component Chemical or CTFA Name | Component Active (%) | Net Concentration in Formulation (%) |
|---|---|---|---|---|
| Incroquat Behenyl TMS (Croda) | 0.7 | behentrimonium methosulfate | 25 | 0.175 |
| | | cetearyl alcohol | 75 | 0.525 |
| Incroquat Behenyl HE (Croda) | 0.3 | behenamidopropyl hydroxyethyl dimonium chloride | 50 | 0.15 |
| | | hexylene glycol | 50 | 0.15 |
| Dow Corning 344 Fluid (Dow Corning) | 0.5 | octamethylcyclo-tetrasiloxane | 77 | 0.385 |
| | | decamethylcyclo-pentasiloxane | 22 | 0.110 |
| Kathon CG (Rohm & Haas) | 0.025 | methylchloroiso-thiazoline | 1.25 | 0.0003 |
| Solan 50 (Croda) | 0.4 | PEG-60 Lanolin | 50 | 0.20 |
| Fragrance | 0.05 | | 100 | 0.05 |
| water | q.s. to 100 | | | |

The required quantities of Incroquat TMS, Incroquat HE, Solan 50 and DC344 Fluid were charged to a heated mixing vessel equipped with a high-speed agitator/impeller. The vessel was heated to a temperature of about 75° to 80° C. to melt the ingredients, and the contents were then mixed at high speed for about 5 minutes. The water was heated in a separate vessel to about the same temperature, i.e., 75° to 80° C., then about 10% to about 15% of the total water charge was added slowly with agitation to the pre-melted melted components in the mixing vessel while the vessel was maintained at 75° to 80° C. Mixing and heating were continued for about another 10 to 15 minutes until the premelted components were totally dispersed in the water phase. The rest of the heated water was added to the mixing vessel and agitation was continued for another 10 minutes. The contents of the mixing vessel were allowed to cool to about 45° C., then the Kathon preservative and fragrance were added. The contents were allowed to further cool to room temperature.

The composition preferably has a pH of about 4 to about 5, and more preferably, between about 4.2 to about 4.4. If necessary, the pH of the composition may be adjusted with an acid such as citric add to bring the pH of the composition to the desired value.

EXAMPLE 2

A hair derange composition having the formula shown in Table 2 was prepared following the procedure of Example 1 except that the Solan 50 was replaced by Tween 20.

TABLE 2

Formula of Example 2

| Ingredient | Ingredient Amount (%) | Component CTFA Name | Component Active (%) | Net Concentration in Formulation (%) |
|---|---|---|---|---|
| Incroquat Behenyl TMS | 0.7 | behentrimonium methosulfate | 25 | 0.175 |
|  |  | cetearyl alcohol | 75 | 0.525 |
| Incroquat Behenyl HE | 0.3 | behenamidopropyl hydroxyethyl dimonium chloride | 50 | 0.15 |
|  |  | hexylene glycol | 50 | 0.15 |
| Dow Corning 344 Fluid | 0.5 | octamethylcyclotetrasiloxane | 77 | 0.385 |
|  |  | decamethylcyclopentasiloxane | 22 | 0.110 |
| Kathon CG | 0.025 | methylchloroisothiazoline | 1.25 | 0.0003 |
| Tween 20 (ICI) | 0.25 | polyoxyethylene (20) sorbitan monolaurate | 100 | 0.25 |
| Fragrance | 0.05 |  | 100 | 0.05 |
| water | q.s. to 100 |  |  |  |

Product Stability

The stability of the compositions of Examples 1 and 2 were assessed by incubating samples of the formulations at several temperatures between about ambient temperature to about 50° C. and periodically measuring the pH and optical appearance of the samples. The samples, which were opaque uniform dispersions, were unchanged in appearance on aging for up to 6 weeks at temperatures from room temperature to 50° C. The pH of the samples was likewise stable over this time period. Likewise the samples were subjected to freeze-thaw stability. Each freeze-thaw cycle comprised cooling the samples to −20° to −10° C., maintaining them at this temperature for about 24 to 36 hours, and returning them to and maintaining them at ambient temperature for an additional 24 to 36 hours. There was no perceptible change in the appearance of the samples on subjecting them to 5 such freeze-thaw cycles.

Detailing Performance

The products of Example 1 and 2 were evaluated for detailing performance on consumer test panelists. Each panelist evaluated the composition of one of the examples against a commercially available control product, "Johnson's Kids No More Tangles" spray on derange marketed by Johnson & Johnson Consumer Products, Inc. The compositions of each example were evaluated by 70 panelists in sequential (blind) nomadic tests. Each panelist was given a spray dispenser package containing the first product (either one of the compositions of Examples 1 or 2 or the control) and they were instructed to apply the product to wet hair after washing. Some of the panelists were also instructed to use the product on dry hair. After one week, the panelists were instructed not to use any derange for three days. They were then given the second sample and instructed to apply it for a second week Panelists were instructed to complete a questionnaire after each use. The following results were determined from the test:

TABLE 3

Detangling Performance

|  | Product of Example 1 | Control | Statistical Significance |
|---|---|---|---|
| Overall Liking of the product (1 = dislike extremely, 9 = like extremely) | 7.21 | 6.84 | >80% |
| Overall detangling ability (1 = poor, 5 = excellent) | 3.67 | 3.54 | <80% |

TABLE 4

Detangling Performance

|  | Product of Example 2 | Control | Statistical Significance |
|---|---|---|---|
| Overall Liking of the product (1 = dislike extremely, 9 = like extremely) | 7.19 | 6.7 | >80% |
| Overall detangling ability (1 = poor, 5 = excellent) | 3.86 | 3.49 | >95% |

The compositions were found by the panelists to improve the manageability of the hair when applied under dry or wet conditions.

Detangling efficacy was also measured on the compositions of the invention in the laboratory as follows:

Detangling was measured on one inch-wide by six inch-long tresses composed of double bleached blond hair purchased from International Hair Importers and Products, Inc. of New York City. The tresses were washed by applying 1 mL of "Tergitol 15S-9" surfactant (Union Carbide Corp.) to the tresses, lathering for two minutes and rinsing for an additional 3 minutes. This washing procedure was repeated a total of three times. The tress was combed out to completely remove tangles. Tangles were reintroduced into the tresses by dunking the tresses in a beaker of water and removing the tresses a total of three times. The tress was clamped in a Dia-Stron 160 Series Miniature Tensile Tester (Dia-stron Ltd., Broomal, Pa.). A plastic comb containing teeth spaced ⅛ inch apart was also clamped to the apparatus. The Tensile Tester measures the load (in grams of force) required to pass the comb through the tress as a function of distance. The apparatus was activated and the comb force vs. distance was recorded. The tress was retangled by dunking in water and the detangling force was measured a total of three times. The average value of the peak force of three consistent readings represents the baseline value to detangle the tress. The tress was once again retangled and the efficacy of a detangler composition was determined by spraying 0.3 gm of the composition on the tress, damping the tress in the Tensile Tester and once again measuring the peak force. The treated tress was once again retangled, and the force to run the comb through the tress was remeasured. An average of three such determinations is taken as the force to detangle the treated tress. The percent comb force reduction was computed as follows.

$$\% \text{ comb force reduction} = \frac{\text{baseline force} - \text{treated force}}{\text{baseline force}} \times 100$$

A graph showing the comb force for a tress evaluating the efficacy of the composition of Example 2 is shown in FIG. 1, which plots the grams of force on the Y axis vs. distance on the X axis. The percent comb force reduction for the compositions of Examples 1 and 2 along with several other compositions is shown in Table 5.

TABLE 5

Comb Force Reduction Data

| Composition | Comb Force Reduction (%) |
|---|---|
| Example 1 | 97.1 |
| Example 2 | 93.1 |
| 0.7% Incroquat Behenyl TMS | 93.5 |
| 0.3% Incroquat Behenyl HE | 84.7 |
| 0.87% Carsoquat SDQ-25 (stearalkonium chloride) | 75.7 |
| 0.25% Adogen 442 PG 75% (dimethyl dialkyl ($C_{14}$—$C_{18}$) ammonium chloride | 73.3 |

The data indicate the excellent detangling ability of the compositions of the invention. The data also suggest that the compositions of Examples 1 and 2 incorporating the quaternary ammonium compounds behentrimonium methosulfate and behenamidopropyl hydroxyethyl dimonium chloride having the longer $C_{22}$ groups are more effective at detangling hair than other compositions comprising species having shorter hydrocarbon chains, i.e., stearalkonium chloride or dimethyl dialkyl ($C_{14}$–$C_{18}$) ammonium chloride.

Eye-irritation

The compositions of this invention also exhibited very low irritation to the eyes and skin. Irritation has been evaluated in accordance with the Invittox Protocol Number 86, the "Trans-epithelial Permeability (TEP) Assay." In accordance with the TEP Assay, the ocular irritation potential of a product can be evaluated by determining its effect on the permeability of a cell layer, as assessed by the leakage of fluorescein through the layer. In accordance with this in vitro method, monolayers of Madin-Darby canine kidney (MDCK) cells are grown to confluence on microporous inserts in a 24well plate containing medium or assay buffer in the lower wells. The irritation potential of a product is evaluated by measuring the damage to the permeability barrier in the cell monolayer following a 15 minute exposure to dilutions of the product. Barrier damage is assessed by the amount of sodium fluorescein that has leaked through to the lower well after 30 minutes, as determined by spectrophotometry. The fluorescein leakage is plotted against the concentration of test material to determine the $EC_{50}$ (the concentration of test material that causes 50% of maximum dye leakage, i.e., 50% damage to the permeability barrier). The test procedure is set forth in Invittox Protocol Number 86 (May 1994), the disclosure of which is hereby incorporated by reference.

Exposure of a layer of MDCK cells grown on a microporous membrane to the test sample is a model for the first event that occurs when an irritant comes in contact with the eye. In vivo, the outermost layers of the corneal epithelium form a selectively permeable barrier due to the presence of tight junctions between cells. On exposure to an irritant, the tight junctions separate, removing the permeability barrier. Fluid is imbibed to the underlying layers of epithelium and to the stroma, causing the collagen lamellae to separate, resulting in opacity. The TEP assay measures the effect of an irritant on the breakdown of tight junctions between cells in a layer of MDCK cells grown on a microporous insert. Damage is evaluated spectrophotometrically, by measuring the amount of marker dye (sodium fluorescein) that leaks through the cell layer and microporous membrane to the lower well. Generally, a passing score is reflected in an $EC_{50}$ of 2.2% or higher. The undiluted composition of Example 1 made in accordance with the present invention showed no leakage and accordingly, had a passing TEP score. This data demonstrates that the compositions of the present invention are expected to be exceptionally mild to the eyes.

EXAMPLES 3–11

The formulations of Examples 3–11 shown in Table 6 are made using the procedure of Example 1.

TABLE 6

Examples 3–11

| Ingredient | weight percent | | | | | | | | |
|---|---|---|---|---|---|---|---|---|---|
| | Ex. 3 | Ex. 4 | Ex. 5 | Ex. 6 | Ex. 7 | Ex. 8 | Ex. 9 | Ex. 10 | Ex. 11 |
| Incroquat Behenyl TMS | — | — | — | — | — | 0.04 | 0.2 | 4 | 2 |
| Incroquat Behenyl HE | 0.02 | 0.2 | 1 | 2 | 4 | 0.3 | 0.3 | 0.3 | 0.3 |
| Dow Corning 344 Fluid | 0.01 | 0.05 | 0.5 | 1 | 2 | 0.5 | 0.5 | 0.5 | 0.5 |

TABLE 6-continued

Examples 3–11

| Ingredient | weight percent | | | | | | | | |
|---|---|---|---|---|---|---|---|---|---|
| | Ex. 3 | Ex. 4 | Ex. 5 | Ex. 6 | Ex. 7 | Ex. 8 | Ex. 9 | Ex. 10 | Ex. 11 |
| Tween 20 | 0.01 | 0.05 | | | 1 | | | | |
| water | q.s. to 100 | q.s. to 100 | q.s. to 100 | q.s. to 100 | q.s. to 100 | q.s. to 100 | q.s. to 100 | q.s. to 100 | q.s. to 100 |

We claim:

1. A hair care composition comprising, based on the weight of the composition:

A. from about 0.01 percent to about 2.0 percent of a quaternary ammonium compound of the formula

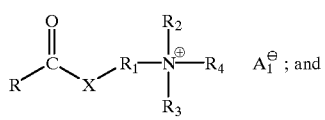

B. from about 0.01 to about 2.0 percent of a silicone compound wherein

R is a substituted or unsubstituted allyl or alkenyl group having from about 19 to about 35 carbon atoms, X is —O— or N—$R_5$, $R_1$ is a substituted or unsubstituted alkylene group having from about 2 to about 6 carbon atoms, $R_2$, $R_3$ and $R_4$ are each independently an alkyl or hydroxyalyl group having from about 1 to about 4 carbon atoms, $R_5$ is H or $CH_3$, and $A_1$ is chloride; bromide; alkylsulfate containing from about one to about two carbon atoms; or mixtures thereof.

2. The composition of claim 1 comprising from about 0.1 to about 1.0 percent by weight of said quaternary ammonium compound.

3. The composition of claim 1 wherein R is an alkyl group having from about 19 to about 21 carbon atoms or mixtures thereof, X is an N—$R_5$ group and $R_5$ is H.

4. The composition of claim 1 wherein said quaternary ammonium compound is selected from:

A. 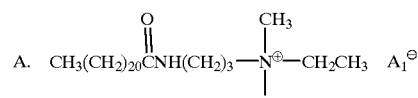

B. 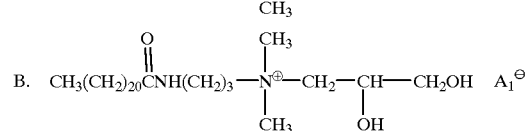

C. 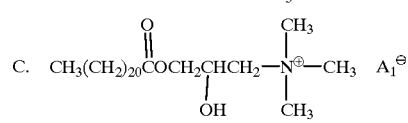

D. 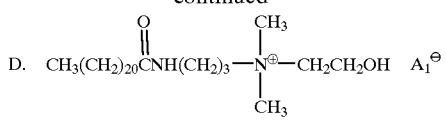

E. and mixtures thereof.

5. The composition of claim 1 wherein said quaternary ammonium compound comprises

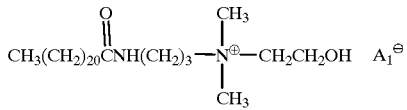

6. The composition of claim 1 comprising from about 0.05 to about 1.0 percent by weight of said silicone compound.

7. The composition of claim 1 wherein said silicone compound is a volatile polydimethyl siloxane having from about 4 to about 6 silicon atoms.

8. The composition of claim 1 which further comprises a glycol or polyol having from about 3 to about 6 carbon atoms.

9. The composition of claim 1 which further comprises from about 0.01 to about 1.0 percent by weight of a nonionic surfactant.

10. The composition of claim 9 wherein said nonionic surfactant is selected from alkoxylated alcohols and alkoxylated polyol esters.

11. The composition of claim 10 wherein said nonionic surfactant is selected from ethoxylated lanolin, ethoxylated sorbitan esters and mixtures thereof.

12. The composition of claim 1 which further comprises from about 0.01 to about 1.0 percent by weight of at least one fatty alcohol having from about 12 to about 36 carbon atoms.

13. The composition of claim 1 in the form of a conditioning shampoo, a rinse-off conditioner, a leave-on conditioner or a hair detangler.

14. The composition of claim 13 in the form of a leave-on conditioner or a hair detangler.

15. The composition of claim 1 having a viscosity and rheology sufficient to permit said composition to be dispensed from a spray dispenser.

16. An article of manufacture comprising the composition of claim 1.

17. The article of manufacture of claim 16 comprising the composition of claim 1 contained within a spray dispenser package or a foam dispenser package.

18. A hair care composition comprising:

A. a first quaternary ammonium compound of the formula

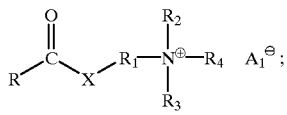

B. a second quaternary ammonium compound of the formula

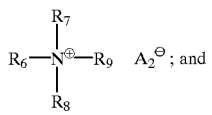

C. from about 0.01 to about 2.0 percent, based on the total weight of the composition, of a silicone compound
wherein
R is a substituted or unsubstituted alkl or alkenyl group having from about 19 to about 35 carbon atoms,
X is —O— or N—$R_5$,
$R_1$ is a substituted or unsubstituted alkylene group having from about 2 to about 6 carbon atoms,
$R_2$, $R_3$ and $R_4$ are each independently an alkyl or hydroxyalkyl group having from about 1 to about 4 carbon atoms,
$R_5$ is H or $CH_3$,
$R_6$ is an alkyl or alkenyl group having from about 12 to about 36 carbon atoms,
$R_7$ is an alkyl or alkenyl group having from about 1 to about 36 carbon atoms or a benzyl group,
$R_8$ and $R_9$ are each independently an alkyl group having from about 1 to about 4 carbon atoms or a benzyl group,
$A_1$ and $A_2$ are each independently chloride; bromide; alkylsulfate containing from about one to about two carbon atoms; or mixtures thereof,
and wherein said first quaternary ammonium compound and said second quaternary ammonium compound together comprise between about 0.01 percent to about 2.0 percent by weight of said composition.

19. The composition of claim 18 wherein $R_6$ is an alkyl group having about 22 carbon atoms and $R_7$, $R_8$ and $R_9$ are each $CH_3$.

20. The composition of claim 18 wherein the weight ratio of said first quaternary ammonium compound to said second quaternary ammonium compound is from about 4:1 to about 1:4.

21. The composition of claim 18 wherein the weight ratio of said first quaternary ammonium compound to said second quaternary ammonium compound is from about 2:1 to about 1:2.

22. A hair care composition comprising:

A. a first quaternary ammonium compound of the formula

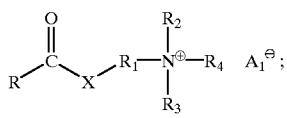

B. a second quaternary ammonium compound of the formula

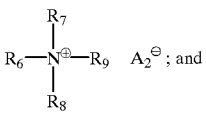

C. based on the total weight of the composition, from about 0.01 percent to about 2.0 percent of a volatile silicone compound
wherein
R is an alkyl or alkenyl group having from about 19 to about 21 carbon atoms,
X is —O— or N—H,
$R_1$ is a substituted or unsubstituted alkylene group having from about 2 to about 6 carbon atoms,
$R_2$, $R_3$ and $R_4$ are each independently alkyl or hydroxyalkyl having from about 1 to about 4 carbon atoms,
$R_6$ is an alkyl or alkenyl group having from about 18 to about 22 carbon atoms,
$R_7$, $R_8$ and $R_9$ are each independently an alkyl group having from about 1 to about 4 carbon atoms or a benzyl group,
$A_1$ and $A_2$ are each independently chloride, bromide; alkylsulfate containing from about one to about two carbon atoms; or mixes thereof,
and wherein said first quaternary ammonium compound and said second quaternary ammonium compound together comprise from about 0.01 percent to about 2.0 percent by weight of said composition.

23. A hair conditioning composition comprising:

A. from about 0.05 percent to about 1.0 percent by weight of a first quaternary ammonium compound of the formula

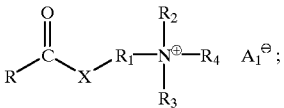

B. from about 0.05 percent to about 1.0 percent by weight of a second quaternary ammonium compound of the formula

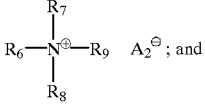

C. from about 0.05 percent to about 1.0 percent by weight of a volatile silicone compound having from about 4 to about 6 silicon atoms,
wherein
R is an alkyl group having about 21 carbon atoms,
X is N—H,
$R_1$ is a substituted or unsubstituted alkylene group having from about 2 to about 6 carbon atoms,
$R_2$, $R_3$ and $R_4$ are each independently alkyl or hydroxyalkyl having from about 1 to about 4 carbon atoms,
$R_6$ is an alkyl group having about 22 carbon atoms,
$R_7$, $R_8$ and $R_9$ are each $CH_3$,
$A_1$ and $A_2$ are each independently chloride; bromide; alkylsulfate containing from about one to about two carbon atoms; or mixtures thereof.

24. Method of conditioning or detangling hair comprising applying to the hair a conditioning or detangling-effective amount of the composition of claim 1.

* * * * *